United States Patent [19]

Keenan

[11] Patent Number: 4,915,226
[45] Date of Patent: Apr. 10, 1990

[54] HYGIENIC DONNING PACKAGING SYSTEM FOR SURGICAL GLOVES

[76] Inventor: Robert Keenan, P.O. Box 178, Dardanelle, Ark. 72834

[21] Appl. No.: 237,050

[22] Filed: Aug. 29, 1988

[51] Int. Cl.4 .................................................. B65D 85/18
[52] U.S. Cl. ................................. 206/438; 2/168; 206/278; 223/111; 604/292
[58] Field of Search ............... 604/292; 128/856, 844, 128/157; 206/278, 438, 439, 363, 364; 223/111; 2/168, 169, 160

[56] References Cited

U.S. PATENT DOCUMENTS

| | | | |
|---|---|---|---|
| 1,085,632 | 2/1914 | Roy | 206/619 |
| 1,756,396 | 4/1930 | Spicer | 206/412 |
| 2,332,857 | 10/1943 | Karg | . |
| 2,533,829 | 12/1950 | Merryweather | 383/24 X |
| 2,857,047 | 10/1958 | Edelson | . |
| 2,932,387 | 4/1960 | Petersen | . |
| 3,097,644 | 7/1963 | Parker | 128/157 |
| 3,326,450 | 6/1967 | Langdon | 206/438 |
| 3,372,799 | 3/1968 | Abildgaard | 206/278 |
| 3,391,855 | 7/1968 | Ansell | 206/278 X |
| 3,638,789 | 2/1972 | Tuszewski | 206/438 |
| 3,797,493 | 3/1974 | Saudek | 206/616 |
| 3,870,150 | 3/1975 | Hummel | 206/438 |
| 3,892,314 | 7/1975 | Semp | 206/363 |
| 3,968,792 | 7/1976 | Small | 128/132 |
| 4,002,276 | 1/1977 | Poncy et al. | 223/111 |
| 4,068,757 | 1/1978 | Casey | 206/363 |
| 4,069,913 | 1/1978 | Harrigan | 206/278 |
| 4,153,054 | 5/1979 | Boone | 128/132 |
| 4,155,494 | 5/1979 | Poncy et al. | 223/111 |
| 4,159,069 | 6/1979 | Poncy et al. | 223/111 |
| 4,275,812 | 6/1981 | Poncy et al. | 206/278 |
| 4,308,864 | 1/1982 | Small et al. | 128/132 |

Primary Examiner—Bryon P. Gehman
Attorney, Agent, or Firm—Foley & Lardner, Schwartz, Jeffery, Schwaab, Mack, Blumenthal & Evans

[57] ABSTRACT

A sterile glove donning system in which an unrolling means, a tab, string or the like, is intertwined with the rolled up cuff of the surgical glove to be donned. As the glove is removed from the package and the package is pulled generally in the direction of unrolling, the unrolling means unrolls the glove along the wearer's forearm. When donning is complete, the package and attached unrolling means are discarded.

10 Claims, 2 Drawing Sheets

HYGIENIC DONNING PACKAGING SYSTEM FOR SURGICAL GLOVES

BACKGROUND OF THE INVENTION

Surgical gloves are universally recognized as a major safeguard against the risk of inadvertent or accidental infection in the administration of medical and dental treatment. Both medical practitioners and patients rely on the protection these gloves provide.

This invention relates to a packaging system for the sale and use of surgical gloves, which allows them to be handled for commercial purposes while keeping them free from contamination. The problems of donning surgical gloves under sterile conditions and the shortcomings of presently available packaged gloves are well known, as explained in detail, for example, in U.S. Pat. No. 4,002,276.

The donning of surgical gloves today usually requires the help of an assistant, who must also be concerned about the maintenance of sterile conditions. These gloves are usually packaged with their cuffs or sleeves turned o rolled downwardly. They must be removed from the package by an assistant, touching only these downwardly turned cuffs. When the glove is donned by pulling or unrolling its cuff or sleeve, the entirety of the previously exposed cuff is on the inside of the glove and touches only the wearer's skin.

Donning the glove my require an assistant to stretch open the cuff, so the wearer may easily insert his fingers into the bottoms or ends of the glove fingers. It is not practical for a wearer to don a glove by himself. It becomes even more impractical for the wearer to put on a second glove, because it must be pulled on with an already surgically gloved hand. The impracticality of putting on surgical gloves without assistance can preclude the administration of first aid or emergency medical treatment under sterile conditions when an assistant is not present. Also, a medical practitioner may find it necessary to delay needed emergency treatment while he or she goes through the awkward procedure of donning gloves unassisted.

Until the wearer's fingers are fully inserted into the glove fingers of presently available gloves, the gloves tend to dangle. This dangling enhances the possibility that the glove will be contaminated by brushing up against, or touching, a non-sterilized surface or object. The wearer may not realize that the glove has become contaminated, and, even if he does, critical time may be lost while a new hygienic glove is donned.

Surgical gloves are usually powdered on their insides to facilitate donning, since they must fit so tightly. This powdering, however, increases the manufacturing complexity of surgical gloves and, accordingly, their price. Also, the powder may accidentally end up on the outside of the glove, from which it must be removed before medical treatment can continue.

Surgical gloves are easily punctured and must, therefore, be readily changeable during medical treatment. When an assistant must be relied upon to change a surgical glove, however, the assistant's glove may become contaminated in the process. If the assistant's glove is already contaminated, it must be replaced before the surgeon's glove can be replaced.

SUMMARY OF THE INVENTION

The surgical glove dispensing package and system of the present invention overcomes the above-described difficulties of donning sterile surgical gloves. A glove-containing package, according to the present invention, may be opened by the intended wearer alone, to expose the rolled up glove. While holding the package by its outside, the wearer may insert his fingers into the glove fingers, which the package exposes, and pull the gloves out of the package. A tab or the like intertwined or interrolled with the glove cuff or sleeve facilitates the unassisted unrolling of the glove. The glove is removed after use in customary way: by pulling it downward from the end of the cuff, inside out, and off the fingers.

The rolled up glove cuffs of the present invention, as mentioned, contain intertwined glove unrolling or unwinding tabs, strings or the like adhesively fixed at one end in a seam of the package. These intertwined tabs are pulled to unroll the glove cuff. When the glove is completely in place on the wearer's hand, the tabs and package free themselves of the glove and are disposed of. The wearer's hand need never touch the outside of the glove and assistance in donning the glove is not needed.

Accordingly, an object of the invention is to provide a surgical glove donning system that allows the wearer himself to don the gloves, while assuring their sterility.

Another object of the invention is to provide an inexpensive, easily usable means for putting on a pair of sterile surgical gloves without touching their outside surfaces.

Another object of the invention is a means to facilitate the unassisted unrolling of a glove cuff and the donning of the glove under sterile conditions.

Still another object of the invention is the manufacture and commercialization of an inexpensive, easy to use, packaged sterile glove.

These and other objects and advantages of the invention will be obvious from the specification and drawings, as set forth or described below.

DETAILED DESCRIPTION OF THE PREFERRED EMBODIMENTS

Figure 1:
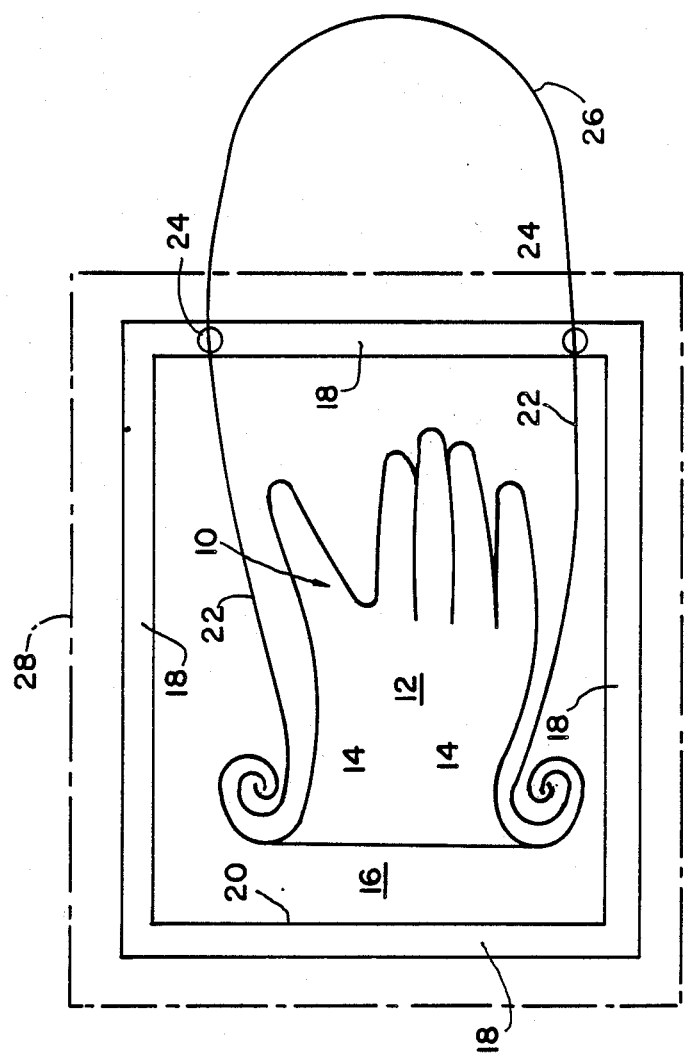
FIG. 1 is a sectional view of the donning system of the invention, illustrating the arrangement of the glove and unrolling tabs.

As seen in FIG. 1, the surgical glove donning system constituting this invention includes a packaged sterile glove 10. The glove is formed of thin latex or other material conventionally used for surgical gloves, such gloves being readily commercially available. The packaged glove includes a finger part 12 and a rolled up cuff 14.

The glove 10 is packaged for sale or storage within envelope or package 16. Package 16, as received by the wearer, is sealed closed on all four of its edges 18 by gluing, heat bonding, or other known sealing means. Various well-known packaging and sealant materials are available for sealing these edges.

A preferred embodiment of the invention, however, utilizes materials that can be sterilized by the application of heat, autoclaving, for example, as a final step in the manufacturing process. The glove contained within the package should, of course, be amenable to sterilization by any such method. The package, just before opening, could also be sterilizable without departing from the concepts of the invention.

Figure 2:
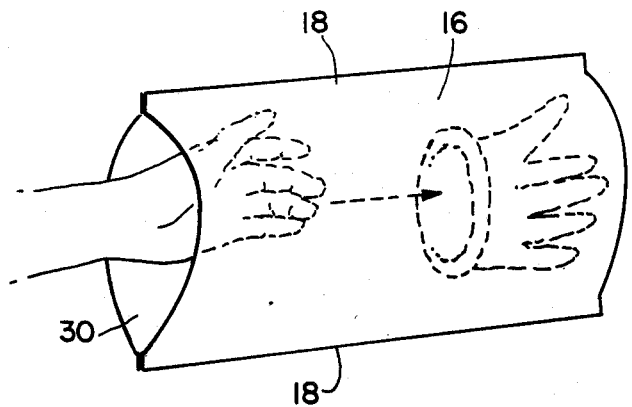
FIG. 2 diagrammatically shows the open configuration of the package in which a sterile glove is contained.

Package 16 is provided with a tear line 20, allowing it to be opened at the end that exposes the interior and fingers of the glove contained therein. The package is opened by squeezing or pushing together the top and bottom edges 18, as seen in FIG. 2, to create a generally oval shaped opening at the end where the tear line is located.

The package is, therefore, preferably made of a metallic or other inflexible material that will so deform and retain its generally oval shaped opening. Such packaging materials and the manufacture of packages therefrom are well known. The dimensions of the packages are such, of course, that the oval shaped opening is large enough for the glove wearer easily to insert his hand through the package opening into the finger part 12 of the glove.

While FIG. 1 shows only one glove in a package, it is understood that a package might contain 10 two gloves. The method of donning two gloves, as described below, is apparent from the description of the invention.

The cuff 14, in its rolled up configuration, is intertwined with unrolling tabs or elements 22. The cuff is unrolled along the wearer's arm as tabs 22 are pulled in a direction away from the finger part 12 of the glove 10.

FIG. 1 illustrates an embodiment of the invention using two tabs or similar means to unroll a surgical glove, once it is removed from the package. It is to be understood, however, that the number of tabs can be varied, or that other means could also be used to unroll the glove. A sleeve for unrolling a surgical stockinette is shown in U.S. Pat. No. 4,153,054, while string unrolling means are shown in U.S. Pat. No. 3,968,792. Either could be used, for example, as a substitute for tab or tabs 22.

Tabs 22 or other unrolling means can be made of various materials, including plastic, cord or rubber. In FIG. 1, each tab 22 extends through, and is sealed by, rightmost sealed edge 18 at region 24 to form a loop 26. This loop could also be separately formed and fixedly attached to the rightmost sealed edge 18 of the package 16. It is not critical to the system that this loop be sterile, although the tabs 22 within the package are sterile.

Once the package is opened, a hand can be inserted into the glove therein. This is shown in FIG. 2. The loop holds the package while the gloved hand is pulled outside of, and away from, the package.

The loop can be placed over any convenient hooking means, for example, over an automobile gear shift lever or a doorknob. The loop can be made of any flexible material and may be of any useful diameter. A convenient loop diameter has been found to be about 3 to 5 inches, but other diameters are equally useful, and the loop may be adjustable. Sufficient slack is provided in tabs 26, so the wearer's hand may be easily withdrawn from the package.

The sterile package 16 may be contained within a dispensing package 28, shown in outline, which need not be sterile. Use of this packaging arrangement permits the commercial handling of the sterile package prior to use without concern about maintaining its sterility.

If two gloves are to be donned, two packages may be opened simultaneously. Once one glove is in place on the wearer, that gloved hand can be inserted into the package, which is sterile, to help remove the other glove.

Figure 3A:
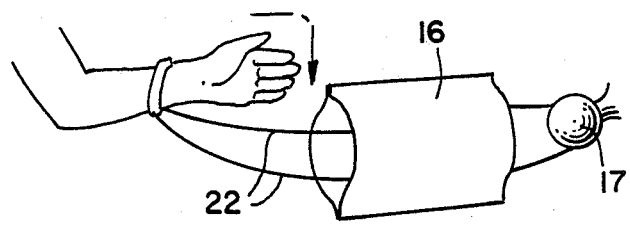
FIG. 3 (a) and (b) is a diagrammatic illustration of a procedure for utilizing the glove donning system of this invention.
Figure 3B:
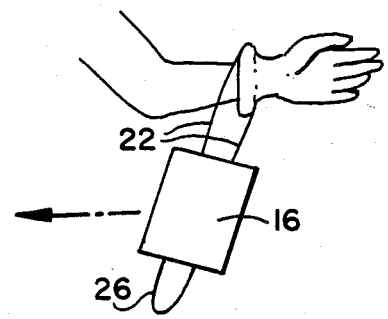

FIG. 3 shows how a glove may be donned. As shown in step (a), the package is opened by the yet ungloved wearer and the hand being inserted into the packaged glove. The loop is placed around a fixed object such as doorknob 17. In step (b), the loop is released, but the glove pulled out and away from the package to free the unrolling tabs or strings 22. Once the cuff is unrolled, the package and tabs are discarded together.

It should be understood that the invention has been described with reference to particular embodiments, but that changes and modifications would not depart from the scope and spirit of the invention as defined by the appended claims.

What is claimed is:

1. A surgical glove donning system comprising:
   a sterile glove with a rolled up cuff; a package in which said glove is contained, said package having a sterile interior;
   means for opening said package to provide access to said glove by the intended wearer;
   unrolling means intertwined with the rolled up cuff of said glove to effect unrolling without touching the glove itself, the unrolling means forming a loop located outside of the package, said unrolling means also attached to the package; whereby the glove is donned by removing it from the package and pulling it in a direction in which the cuff is to be unrolled.

2. The system of claim 1 in which the unrolling means are secured to said glove and the interior of said package.

3. The system of claim 1 in which two gloves are contained in said package.

4. The system of claim 1 in which said package has a sterile exterior.

5. The system of claim 4 in which said package having a sterile exterior is contained in an outer package.

6. The system of claim 5 in which said outer package includes means for opening and removing said sterile package.

7. The system of claim 1 in which said package is made of metal foil.

8. The system of claim 7 in which said package further includes a tear away portion for opening said package and exposing said glove for donning.

9. The system of claim 1 in which said loop is about 3–5 inches in diameter.

10. The system of claim 1, in which a loop is attached to the exterior of said package.

* * * * *